(12) United States Patent
Oh et al.

(10) Patent No.: US 7,635,746 B2
(45) Date of Patent: Dec. 22, 2009

(54) DIAMINE COMPOUND CONTAINING TRIAZINE GROUP, POLYAMIC ACID SYNTHESIZED FROM THE DIAMINE COMPOUND AND LC ALIGNMENT FILM PREPARED FROM THE POLYAMIC ACID

(75) Inventors: Jae Min Oh, Suwon-Shi (KR); Bum Jin Lee, Seongnam-Shi (KR); Moo Young Lee, Gunpo-Shi (KR); O Bum Kwon, Seoul (KR); Joon Suk Oh, Kunpo-Shi (KR); Dong Won Park, Seoul (KR); Chul Hee Kim, Seongnam-Shi (KR)

(73) Assignee: Cheil Industries Inc., Kumi-Shi (KR)

( * ) Notice: Subject to any disclaimer, the term of this patent is extended or adjusted under 35 U.S.C. 154(b) by 0 days.

(21) Appl. No.: 10/525,671

(22) PCT Filed: Jan. 20, 2004

(86) PCT No.: PCT/KR2004/000102

§ 371 (c)(1),
(2), (4) Date: Sep. 12, 2005

(87) PCT Pub. No.: WO2004/090017

PCT Pub. Date: Oct. 21, 2004

(65) Prior Publication Data

US 2006/0149028 A1    Jul. 6, 2006

(30) Foreign Application Priority Data

Apr. 9, 2003    (KR) .................. 10-2003-0022261

(51) Int. Cl.
    *C08G 69/08*    (2006.01)
(52) U.S. Cl. .............. 528/310; 428/473.5; 428/1.1; 428/1.2; 528/332; 528/424; 528/353; 528/125
(58) Field of Classification Search .............. 428/473.5, 428/1.1, 1.2; 528/310, 332, 424, 353, 125
    See application file for complete search history.

(56) References Cited

U.S. PATENT DOCUMENTS

| | | | | |
|---|---|---|---|---|
| 3,700,665 A | * | 10/1972 | Seltzer et al. ............... | 544/180 |
| 3,729,448 A | * | 4/1973 | Seltzer et al. ............... | 528/228 |
| 3,944,547 A | * | 3/1976 | Model et al. ................. | 544/216 |
| 4,558,117 A | | 12/1985 | Nakano et al. | |
| 5,756,649 A | * | 5/1998 | Mizushima et al. ......... | 528/353 |
| 6,159,654 A | * | 12/2000 | Machida et al. .......... | 430/270.1 |
| 6,316,170 B2 | * | 11/2001 | Kawamonzen et al. ...... | 430/330 |
| 6,355,357 B1 | | 3/2002 | Takahashi et al. | |
| 2004/0188653 A1 | * | 9/2004 | Kataoka et al. ......... | 252/299.01 |

FOREIGN PATENT DOCUMENTS

| | | |
|---|---|---|
| JP | 6-136120 | 5/1994 |
| JP | 2000-186143 | 7/2000 |
| JP | 2002-80596 | 3/2002 |
| WO | WO 2004/090017 A1 | 10/2004 |

OTHER PUBLICATIONS

Butuc et al "Ordered heterocyclic copolymers . . . " Journal of polymer Sci, Pol. chem ed, vol. 22, 503-507(1984).*
Melissaris et al New crosslinkable polyimides . . . Eur. Polymer Journal , vol. 25 455-460 (1989).*
USPTO structure search.*
English Translation of the Abstract of JP 6-136120.
English Translation of the Abstract of JP 2002-80596.
International Search Report for WO 04/090017 dated Apr. 29, 2004.
International Preliminary Report on Patentability of the International Searching Authority for PCT/KR2004/000102 issued Oct. 14, 2005.
Written Opinion of the International Searching Authority for PCT/KR2004/000102 mailed Apr. 29, 2004.

* cited by examiner

*Primary Examiner*—James Seidleck
*Assistant Examiner*—Gregory Listvoyb
(74) *Attorney, Agent, or Firm*—Paul T. Clark; Clark & Elbing LLP

(57) ABSTRACT

Diamine compound containing specific triazine group, polyamic acid obtained by reacting the diamine compound and tetracarboxylic dianhydride, and liquid crystal alignment film obtained by coating and imidizing the polyamic acid. The liquid crystal alignment film has good heat-resistance, high transparency in visible light region and improved voltage holding ratio. Also, pretilt angle is easily controlled over broad range.

12 Claims, 1 Drawing Sheet

DIAMINE COMPOUND CONTAINING TRIAZINE GROUP, POLYAMIC ACID SYNTHESIZED FROM THE DIAMINE COMPOUND AND LC ALIGNMENT FILM PREPARED FROM THE POLYAMIC ACID

CROSS-REFERENCE TO RELATED APPLICATIONS

This application is the National Stage of International Application No. PCT/KR2004/000102 filed Jan. 20, 2004, which was published in English under PCT Article 21(2). This application also claims benefit of Korea Provisional Application No. 10-2003-0022261, filed Apr. 9, 2003.

TECHNICAL FIELD

The present invention relates to a diamine compound containing a triazine moiety, a polyamic acid prepared from the diamine compound, and a liquid crystal alignment film produced from the polyamic acid. More particularly, the present invention relates to a diamine compound containing a specific triazine moiety, a polyamic acid prepared by reacting a diamine component (a) including the diamine compound and an acid dianhydride (b), and a liquid crystal alignment film produced by imidizing the polyamic acid.

BACKGROUND ART

Conventional polyimide resins for liquid crystal alignment films are prepared from the polycondensation of aromatic acid dianhydrides, such as pyromellitic acid dianhydride (PMDA) and biphthalic acid dianhydride (BPDA), and aromatic diamines, such as p-phenylenediamine (p-PDA), m-phenylenediamine (m-PDA), 4,4-methylenedianiline (MDA), 2,2-bisaminophenylhexafluoropropane (HFDA), m-bisaminophenoxydiphenylsulfone (m-BAPS), p-bisaminophenoxydiphenylsulfone (p-BAPS), 4,4-bisaminophenoxyphenylpropane (BAPP), 4,4-bisaminophenoxyphenylhexafluoropropane (HF-BAPP) and the like.

Polyimide liquid crystal alignment films produced from the conventional aromatic acid dianhydrides and aromatic diamines are excellent in thermal stability, chemical resistance and mechanical properties, but are poor in electrooptical properties, as well as in transparency and solubility, due to the formation of a charge transfer complex. In efforts to solve these problems, Japanese Patent Laid-open No. Hei 11-84319 discloses a polyimide-based liquid crystal alignment film into which an alicyclic acid dianhydride monomer or an alicyclic diamine is introduced, and Japanese Patent Laid-open No. Hei 06-136122 discloses a polyimide-based liquid crystal alignment film having an increased pretilt angle of a liquid crystal and improved stability produced by using a functional diamine having a side chain or a functional acid dianhydride having a side chain.

According to a study undertaken by the present inventors, since the conventional polyimide-based alignment films use polyimides unsuitable for surface tension and polarity to obtain a high pretilt angle of liquid crystals, the spreadability of liquid crystals upon injection of the liquid crystals is poor, causing many defects in the final liquid crystal alignment film, and the controllable range of the pretilt angle is not increased to a satisfactory level.

As demand for liquid crystal display devices has recently increased, there is a continuing need for high quality display devices. Further, as technologies for large-scaled liquid crystal display devices have made remarkable progress, alignment films having a high productivity are more and more required. Thus, there is an urgent need in the art to develop a liquid crystal alignment film which facilitates the pretilt angle control of a liquid crystal over a broad range of angles and has few defects when applied to LCD fabrication processes and shows excellent electrooptical properties, high reliability and superior spreadability of a liquid crystal.

DISCLOSURE OF THE INVENTION

The present inventors have earnestly and intensively conducted research to solve the above-mentioned problems. As a result, the present inventors have found that an alignment film produced from the imidization of a polyamic acid, which is prepared by using a novel specific diamine compound containing a highly polar triazine moiety, can make a desired pretilt angle of a liquid crystal within the range of 1~90° and shows excellent alignment properties of a liquid crystal, excellent electrooptical properties, superior printability and superior spreadability of a liquid crystal, thus accomplishing the present invention.

Therefore, it is a feature of the present invention to provide a liquid crystal alignment film having superior printability, superior spreadability of a liquid crystal, a high pretilt angle of a liquid crystal and few defects when applied to LCD fabrication processes, which is produced by using a novel specific triazine-based diamine compound.

In accordance with the feature of the present invention, there is provided a diamine compound containing a triazine moiety, represented by Formula 1 below:

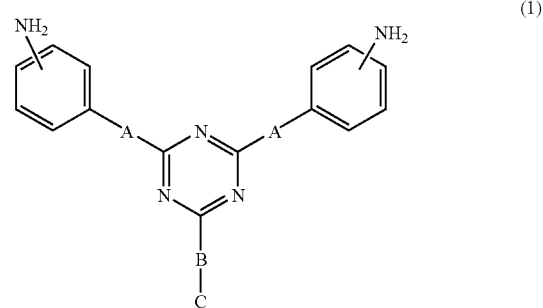

wherein A is a direct bond, —O— or —COO—; B is a direct bond, —O—, —COO—, —CONH— or —OCO—; and C is a $C_{1\sim30}$ linear, branched or cyclic monovalent organic group, or a combined form thereof.

In accordance with the feature of the present invention, there is further provided a polyamic acid prepared by reacting a diamine component (a) and an acid dianhydride (b), the diamine component including 0.1 mole % or above of the diamine compound of Formula 1 based on 100 mole % of the diamine component.

In accordance with the feature of the present invention, there is yet further provided a liquid crystal alignment film produced by dissolving the polyamic acid in a solvent to obtain a liquid crystal aligning agent, coating the aligning agent onto a substrate, and entirely or partly imidizing the coating.

BRIEF DESCRIPTION OF THE DRAWINGS

The above and other objects, features and other advantages of the present invention will be more clearly understood from the following detailed description taken in conjunction with the accompanying drawings, in which.

BEST DESCRIPTION FOR CARRYING OUT THE INVENTION

Figure 1:
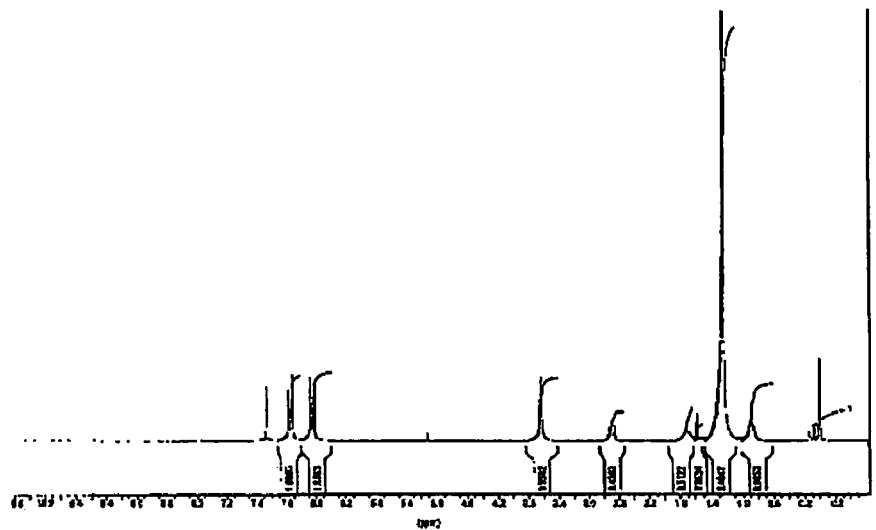
FIG. 1 is a $^1$H-NMR spectrum of a diamine compound prepared in Preparative Example 3 of the present invention.

The present invention will now be described in more detail.

Preferred triazine moiety-containing diamine compounds of Formula 1 are those wherein the substituent C is a linear or branched aliphatic hydrocarbon group, a saturated cyclic hydrocarbon group, a cyclic hydrocarbon group containing at least one carbon-carbon double bond, a fused saturated or unsaturated cyclic hydrocarbon group, or a group selected from the following groups:

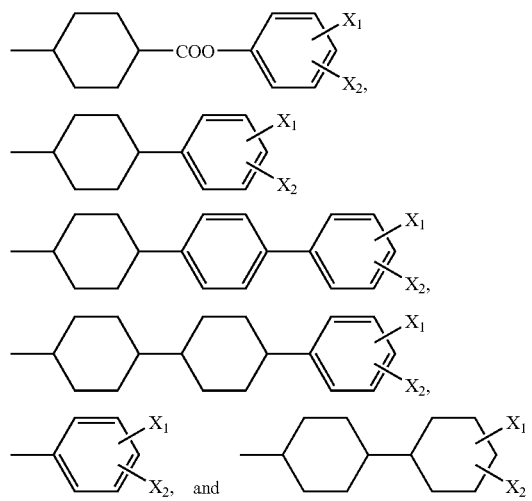

wherein $X_1$ and $X_2$ are each independently —H, —CH$_3$, —CF$_3$, —F, —Br, —Cl, —CN, —OH, or —NO$_2$.

The aliphatic hydrocarbon group, saturated cyclic hydrocarbon group, cyclic hydrocarbon group containing at least one carbon-carbon double bond, and fused saturated or unsaturated cyclic hydrocarbon group may be substituted with at least one group selected from the group consisting of —H, —CH$_3$, —CF$_3$, —F, —Br, —Cl, —CN, —OH and —NO$_2$.

As diamine compounds usable in the present invention, there are exemplified the following compounds:

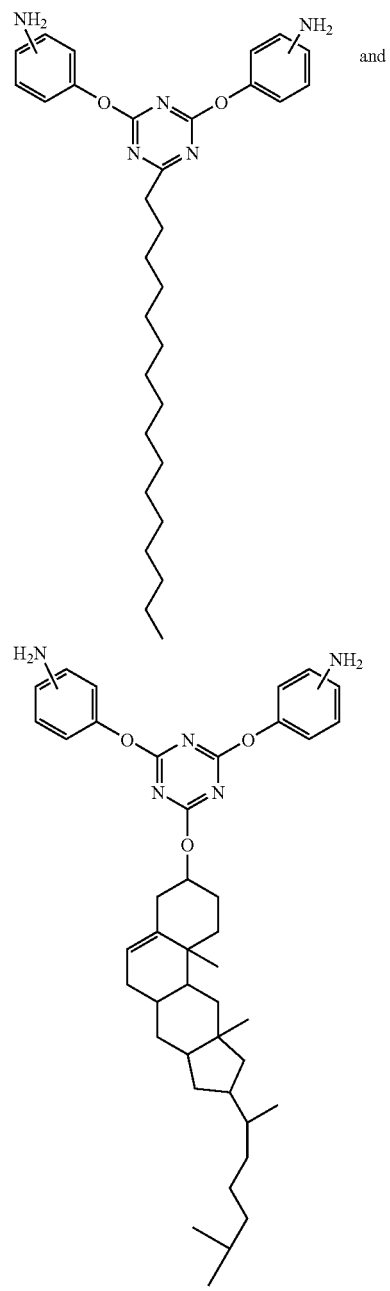

The present invention also provides a polyamic acid having a repeating unit represented by Formula 2 below:

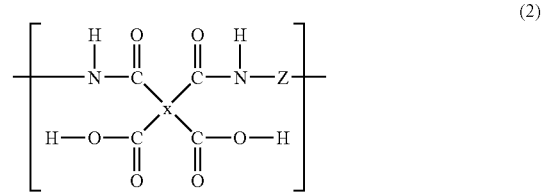

(2)

wherein x is a tetravalent aromatic or alicyclic organic group, and z is a divalent organic group originating from the diamine compound of Formula 1 or a divalent organic group originating from an aromatic or polysiloxane-based diamine.

Specifically, the polyamic acid of the present invention is prepared by reacting a diamine component (a) and an acid dianhydride (b), the diamine component including 0.1 mole % or above of the diamine compound of Formula 1 based on 100 mole % of the diamine component.

The present inventors have found that the use of a specific diamine compound containing a triazine moiety as the diamine component for the preparation of the polyamic acid widens the controllable range of a pretilt angle of the final polyimide, facilitates the control of the pretilt angle, and allows to exhibit excellent alignment properties.

The content of the diamine compound of Formula 1 in the diamine component (a) is in the range of 0.1~100 mole %, preferably 1~60 mole %, and more preferably 2~30 mole %, based on 100 mole % of the diamine component (a).

The pretilt angle is dependent on the content of the diamine compound of Formula 1. Depending on the mode of liquid crystal display devices, the diamine compound may be used alone to prepare the polyamic acid, after which the polyamic acid is imidized to produce a liquid crystal alignment film. Optionally, there may be further added an aromatic diamine compound and/or a polysiloxane-based diamine compound represented by Formulae 3 and 4 below, respectively:

$$H_2N\text{—}Y\text{—}NH_2 \quad (3)$$

wherein Y is a divalent aromatic organic group,

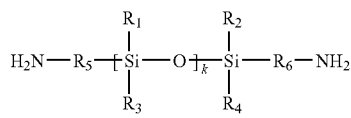

wherein $R_1$, $R_2$, $R_3$ and $R_4$ are each independently a $C_{1\sim10}$ alkyl, alkoxy or aryl group, and $R_5$ and $R_6$ are each independently a $C_{1\sim10}$ alkylene group.

In Formula 3 above, Y is preferably a divalent organic group selected from the group consisting of the following groups:

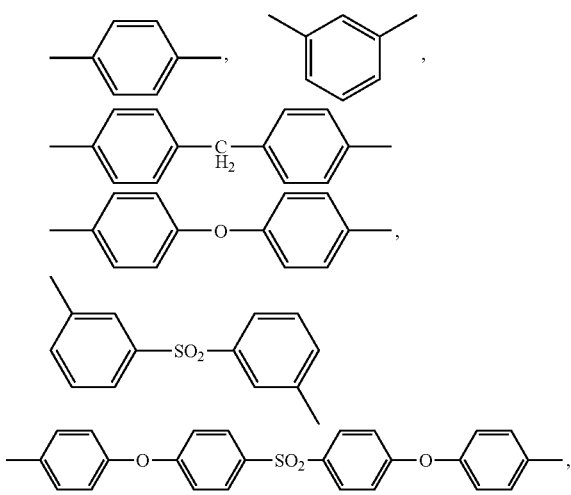

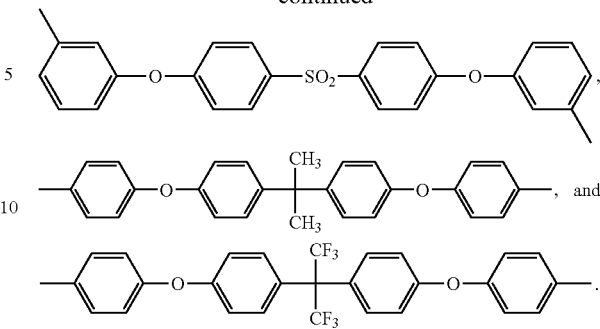

Preferred examples of aromatic cyclic diamine compounds of Formula 3 include, but are not limited to, p-phenylenediamine (p-PDA), 4,4-methylenedianiline (MDA), 4,4-oxydianiline (ODA), m-bisaminophenoxydiphenylsulfone (m-BAPS), p-bisaminophenoxydiphenylsulfone (p-BAPS), 2,2-bisaminophenoxyphenylpropane (BAPP), 2,2-bisaminophenoxyphenyl hexafluoropropane (HF-BAPP) and the like.

A preferred example of polysiloxane-based diamine compounds of Formula 4 includes the following compound:

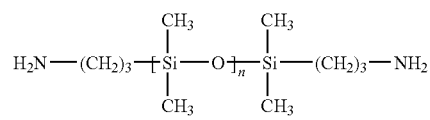

wherein n is an integer of 1 to 10.

The addition of the aromatic diamine compound of Formula 3 is advantageous in that the final polyimide liquid crystal alignment film has an increased mechanical strength. The addition of the polysiloxane-based diamine compound of Formula 4 is advantageous in that the final polyimide liquid crystal alignment film has improved adhesiveness, leading to increased mechanical strength.

The amount of the aromatic cyclic diamine, the polysiloxane-based diamine or a mixture thereof used is in the range of 0~99.9 mole %, preferably 40~99 mole % and more preferably 70~98 mole %, based on the total amount of the diamine component (a). In the case of the mixture of the aromatic cyclic diamine and the polysiloxane-based diamine, the mixing molar ratio of the aromatic cyclic diamine to the polysiloxane diamine is between 0.5:99.5 and 99.5:0.5.

The acid dianhydride component (b) used for the preparation of the polyamic acid according to the present invention is an aromatic cyclic acid dianhydride represented by Formula 5 below:

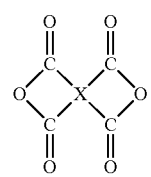

wherein X is a tetravalent aromatic cyclic organic group; an alicyclic acid dianhydride represented by Formula 6 below:

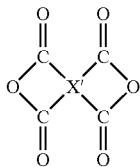
(6)

wherein X' is a tetravalent alicyclic organic group; or a mixture thereof.

Preferred is a mixture of the aromatic cyclic acid dianhydride and the alicyclic acid dianhydride wherein the mixing molar ratio of the aromatic cyclic acid dianhydride to the alicyclic acid dianhydride is between 1:99 and 99:1.

The substituent X in Formula 5 above is preferably a tetravalent aromatic cyclic organic group selected from the following groups:

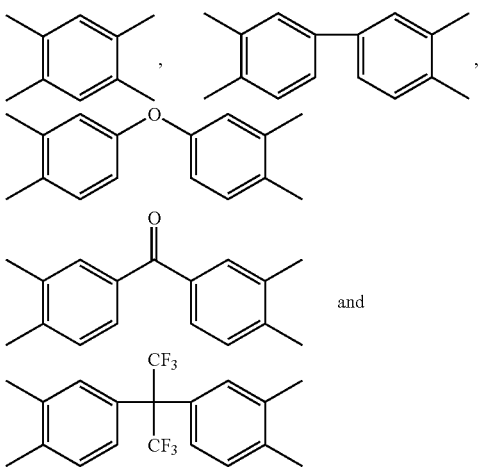

The substituent X' in Formula 6 is preferably a tetravalent alicyclic organic group selected from the following groups:

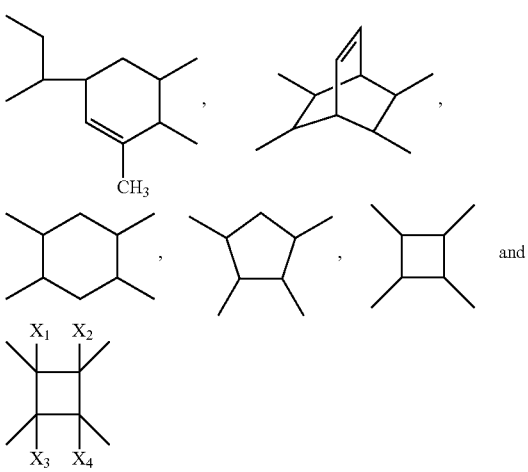

wherein $X_1$, $X_2$, $X_3$ and $X_4$ are each independently —H, —$CH_3$, —$CF_3$, —F, —Br, —Cl, —CN, —OH or —$NO_2$.

The aromatic cyclic acid dianhydride which is used to prepare the polyamic acid of the present invention causes an alignment film (applied to a thickness of about 0.1 μm) to be resistant to a rubbing process, which is carried out in order to drive liquid crystals in one direction, to be heat resistant to high temperature processes (200° C. or above), and to be resistant to chemicals.

Examples of aromatic cyclic acid dianhydrides include, but are not limited to, pyromellitic acid dianhydride (PMDA), biphthalic acid dianhydride (BPDA), oxydiphthalic acid dianhydride (ODPA), benzophenonetetracarboxylic acid dianhydride (BTDA), hexafluoroisopropylidene diphthalic acid dianhydride (6-FDA) and the like.

The content of the aromatic cyclic acid dianhydride is preferably in the range of 1~99 mole %, preferably 10~80 mole % and more preferably 10~50 mole %, based on the total amount of the acid dianhydrides. When the content of the aromatic cyclic acid dianhydride is less than the range defined above, the final alignment film is poor in mechanical properties and heat resistance. On the other hand, when the content of the aromatic cyclic acid dianhydride exceeds the range, the electrical properties, such as voltage holding ratio, of the final alignment film is worsened.

The addition of the alicyclic acid dianhydride which is used to prepare the polyamic acid according to the present invention solves problems such as insolubility in common organic solvents, low transmittance in the visible light region due to the formation of a charge transfer complex, poor electrooptical properties due to high polarity, resulting from the molecular structure of the polyamic acid, etc. Examples of the alicyclic acid dianhydride include, but are not limited to, 5-(2,5-dioxotetrahydrofuryl)-3-methylcyclohexene-1,2-dicarboxylic acid dianhydride (DOCDA), bicyclooctene-2,3,5,6-tetracarboxylic acid dianhydride (BODA), 1,2,3,4-cyclobutane tetracarboxylic acid dianhydride (CBDA), 1,2,3,4-cyclopentanetetracarboxylic acid dianhydride (CPDA), 1,2,4,5-cyclohexanetetracarboxylic acid dianhydride (CHDA) and the like.

The content of the alicyclic acid dianhydride is in the range of 1~99 mole %, preferably 20~90 mole % and more preferably 50~90 mole %, based on the total amount of the acid dianhydrides.

The polyamic acid of the present invention exhibits good solubility in general aprotic polar solvents such as N-methyl-2-pyrrolidone (NMP), γ-butyrolactone (GBL) dimethylformamide (DMF), dimethylacetamide (DMAc) and tetrahydrofuran (THF). It was found by the present inventors that such increase in solubility is attributed to the introduction of the alicyclic acid dianhydride, and the presence of the main chain containing a highly polar triazine moiety and side chains expanding the free volume of the polymer in the functional diamine. As liquid crystal display devices have recently become large-sized and need to have high resolution and high quality, the printability of aligning agents has been gaining importance. Under these circumstances, good solubility in solvents and high polarity of the polyamic acid are very critical factors and have a positive effect upon the printability on a substrate when the polyamic acid is applied to liquid crystal alignment films.

The polyamic acid of the present invention has a number average molecular weight ranging from 10,000 to 500,000 g/mol and preferably 10,000 to 300,000 g/mol. The polyamic acid has a glass transition temperature of 200~350° C., which is dependent on the imidization rate or the structure of the polyamic acid.

The polyimide-based liquid crystal alignment film is produced by dissolving the polyamic acid in a given solvent to obtain a liquid crystal aligning agent, coating the aligning agent onto a substrate, and entirely or partially imidizing the coating.

Examples of solvents used to produce the liquid crystal aligning agent include, but are not specially limited to, aprotic polar solvents such as N-methyl-2-pyrrolidone (NMP), γ-butyrolactone (GBL), dimethylformamide (DMF), dimethylactamide (DMAc), tetrahydrofuran (THF) and the like.

After coating, the imidization reaction is carried out in an oven or on a hot plate at a high temperature of 180~250° C. for 5~30 minutes. The imidization rate may be varied within the range of 30~99% according to the intended purpose.

The liquid crystal alignment film produced by imidizing the polyamic acid has a high transmittance of 90% or more in the visible light region, excellent alignment properties of a liquid crystal, and facilitates the pretilt angle control of a liquid crystal within the range of 1~90°. In addition, since the liquid crystal alignment film of the present invention contains the diamine compound of Formula 1, it has improved electrooptical properties, e.g., a low refractive index and a low dielectric constant.

Hereinafter, the constitution and effects of present invention will be described in more detail with reference to the following preferred examples and comparative example. However, these examples are given for the purpose of illustration and are not to be construed as limiting the scope of the invention.

PREPARATIVE EXAMPLE 1

Preparation of
2,4-dichloro-6-hexadecyl-1,3,5-triazine 2.7 g of magnesium was added to 200 ml of tetrahydrofuran and stirred until the magnesium was completely dissolved. To the solution was added dropwise a solution of bromohexadecane (31.1 g) in tetrahydrofuran (200 ml). Thereafter, the resulting solution was heated to 65° C. and reacted for 6 hours with stirring. The reaction solution was slowly added dropwise to a solution of cyanuric chloride (15 g) in tetrahydrofuran (250 ml), and reacted for 12 hours. After completion of the reaction, the resulting solution was evaporated under reduced pressure to obtain a concentrate and then the concentrate was purified by distillation in vacuo to yield pure 2,4-dichloro-6-hexadecyl-1,3,5-triazine.

PREPARATIVE EXAMPLE 2

Preparation of
2,4-dinitrophenoxy-6-hexadecyl-1,3,5-triazine

A solution of the compound (9.7 g) prepared in Preparative Example 1 in dichloromethane (100 ml) was added to an aqueous solution of 21.62 g of 4-nitrophenol and 6.22 g of sodium hydroxide. The resulting solution was refluxed for 24 hours. After the reaction, the aqueous layer was separated and the dichloromethane layer was extracted with 1N aqueous solution, washed with ultrapure water several times, dried over magnesium sulfate, and evaporated under reduced pressure to obtain a crude product. The crude product was processed by anhydrous recrystallization to afford 2,4-dinitrophenoxy-6-hexadecyl-1,3,5-triazine as a white solid.

PREPARATIVE EXAMPLE 3

Figure 2:
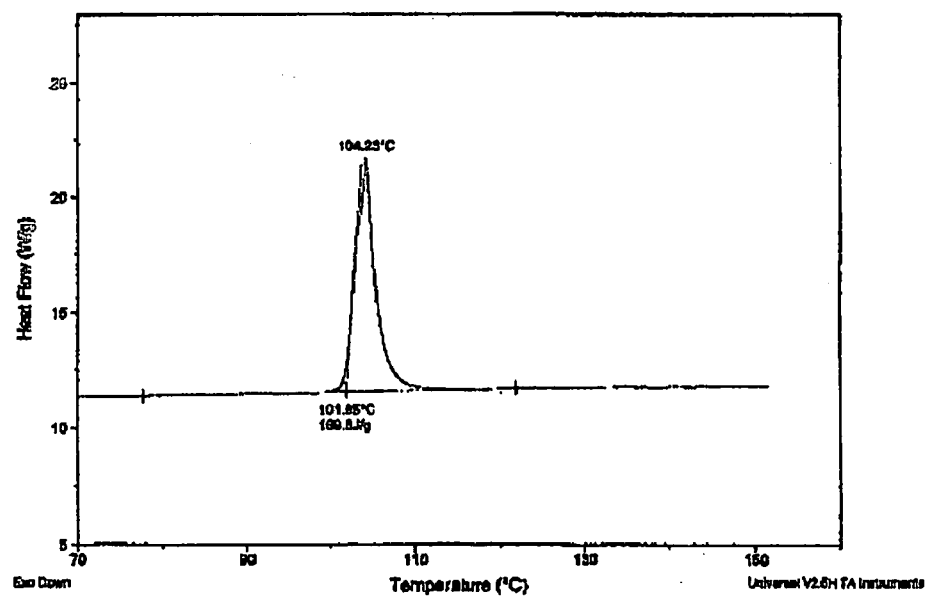
FIG. 2 is a differential scanning calorimetry (DSC) thermogram of a diamine compound prepared in Preparative Example 3 of the present invention.

Preparation of
2,4-diaminophenoxy-6-hexadecyl-1,3,5-triazine 14.5 g of 2,4-dinitrophenoxy-6-hexadecyl-1,3,5-triazine prepared in Preparative Example 2 was dissolved in 300 ml of tetrahydrofuran, and then 1.4 g of Pd/C was added thereto. Hydrogen gas at 50 psi was fed to the mixture, and then reacted at 60° C. for 12 hours. After the reaction, the reaction mixture was filtered to remove palladium, and evaporated under reduced pressure to obtain a crude product. The crude product was recrystallized to afford pure 2,4-diaminophenoxy-6-hexadecyl-1,3,5-triazine as a white solid. The final product was relatively stable under ambient conditions. The structure of the final product was identified through $^1$H-NMR spectrum, and the differential scanning calorimetry (DSC) was performed (see, FIGS. 1 and 2).

EXAMPLE 1

0.95 moles of 4,4-methylenedianiline as a diamine component and 0.05 moles of 2,4-diaminophenoxy-6-hexadecyl-1,3,5-triazine prepared in Preparative Example 3 were charged into a four-neck flask equipped with a stirrer, a thermostat, a nitrogen injection device and a condenser while passing nitrogen, and then N-methyl-2-pyrrolidone (NMP) was dissolved therein. To the resulting solution was added 0.5 moles of 5-(2,5-dioxotetrahydrofuryl)-3-methylcyclohexane-1,2-dicarboxylic acid dianhydride (DOCDA) in a solid form and 0.5 moles of pyromellitic acid dianhydride (PMDA) as acid dianhydride components. The resulting mixture was vigorously stirred. At this time, the solid content was 15% by weight. The mixture was reacted at a temperature lower than 25° C. for 24 hours to prepare a polyamic acid solution (PAA-1) (molecular weight: 50,000~150,000 g/mol).

The polyamic acid solution was applied onto an ITO glass substrate to a thickness of 0.1 μm, and cured at 210° C. for 10 minutes to produce a liquid crystal alignment film. After the liquid crystal alignment film was subjected to a rubbing process, the alignment properties and the pretilt angle of the liquid crystal were measured. In order to evaluate the printability of the liquid crystal alignment film, after the alignment film was applied onto an ITO glass substrate, the spreadability and curling properties at the ends were observed. Specifically, the surface of the alignment film was rubbed by means of a rubbing machine, two substrates were arranged parallel to each other in such a manner that the rubbing direction of the each substrate was reverse, and the two substrates were sealed while maintaining a cell gap of 80 μm to fabricate a liquid crystal cell. The liquid crystal cell was filled with a liquid crystalline compound (Merk licristal). The alignment properties of the liquid crystal were observed under an orthogonally polarlized optical microscope. The pretilt angle of the liquid crystal was measured by a crystal rotation method. The results are shown in Table 1 below.

In order to examine the electrical properties, a polyamic acid solution was applied onto the surface of an ITO-patterned glass substrate to a thickness of 0.1 μm, two substrates were arranged orthogonally to each other in such a manner that the rubbing direction-of the each substrate was perpendicular (90°, and the two substrates were sealed while maintaining a cell gap of 5 μm to fabricate a test cell. The voltage holding ratio was measured, and the results are shown in Table 1 below.

EXAMPLE 2

A polyamic acid (PAA-2) was prepared in the same manner as in Example 1, except that 0.9 moles of 4,4-methylenedianiline and 0.1 moles of 2,4-diaminophenoxy-6-hexadecyl-1,3,5-triazine were used. The alignment properties, the pretilt angle and the voltage holding ratio were measured. The results are shown in Table 1 below.

EXAMPLE 3

A polyamic acid (PAA-3) was prepared in the same manner as in Example 1, except that 0.5 moles of cyclobutane dianhydride was used instead of 0.5 moles of 5-(2,5-dioxotetrahydrofuryl)-3-methylcyclohexane-1,2-carboxylic acid dianhydride (DOCDA). The alignment properties, the pretilt angle and the voltage holding ratio were measured. The results are shown in Table 1 below.

EXAMPLE 4

A polyamic acid (PAA-4) was prepared in the same manner as in Example 2, except that 0.5 moles of cyclobutane dianhydride was used instead of 0.5 moles of 5-(2,5-dioxotetrahydrofuryl)-3-methylcyclohexane-1,2-carboxylic acid dianhydride (DOCDA). The alignment properties, the pretilt angle and the voltage holding ratio were measured. The results are shown in Table 1 below.

EXAMPLE 5

A polyamic acid (PAA-5) was prepared in the same manner as in Example 1, except that 4,4-methylenedianiline was not used, and 1.0 mole of 2,4-diaminophenoxy-6-hexadecyl-1,3,5-triazine was used. The alignment properties, the pretilt angle and the voltage holding ratio were measured. The results are shown in Table 1 below.

COMPARATIVE EXAMPLE 1

A polyamic acid (PAA-6) was prepared in the same manner as in Example 2, except that 2,4-diamino-1-hexadecyloxybenzene was used instead of 2,4-diaminophenoxy-6-hexadecyl-1,3,5-triazine. The alignment properties, the pretilt angle and the voltage holding ratio were measured as described in Example 2. The results are shown in Table 1 below.

TABLE 1

| Sample | Pretilt angle | Voltage holding ratio (%) Room Temp. | Voltage holding ratio (%) 60° C. | Printability | Alignment properties | Spreadability |
|---|---|---|---|---|---|---|
| PAA-1 | 5.3 | 99.5 | 98.2 | Good | Good | Good |
| PAA-2 | 8.1 | 99.3 | 97.6 | Good | Good | Good |
| PAA-3 | 4.8 | 99.1 | 97.3 | Good | Good | Good |
| PAA-4 | 7.7 | 99.1 | 95.9 | Good | Good | Good |
| PAA-5 | 89.8 | 99.0 | 94.5 | Poor | Good | Good |
| PAA-6 | 6.9 | 98.8 | 93.7 | Good | Good | Poor |

As can be seen from Table 1, the liquid crystal alignment films according to the present invention have excellent electrooptical properties, e.g., high voltage holding ratio, and the pretilt angle of liquid crystals can be easily controlled.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A diamine compound containing a triazine moiety, represented by Formula 1 below:

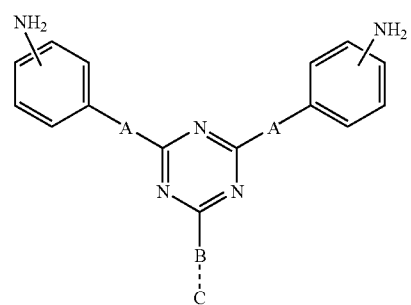

wherein A is —O— or —COO—; B is a direct bond; and C is a $C_{1-30}$ linear or branched aliphatic hydrocarbon group, a saturated cyclic hydrocarbon group, or a fused saturated or unsaturated cyclic hydrocarbon group which is unsubstituted or substituted with at least one group selected from the group consisting of —H, —$CH_3$, —$CF_3$, —F, —Br, —Cl, —CN, —OH and —$NO_2$; or a group selected from the following groups:

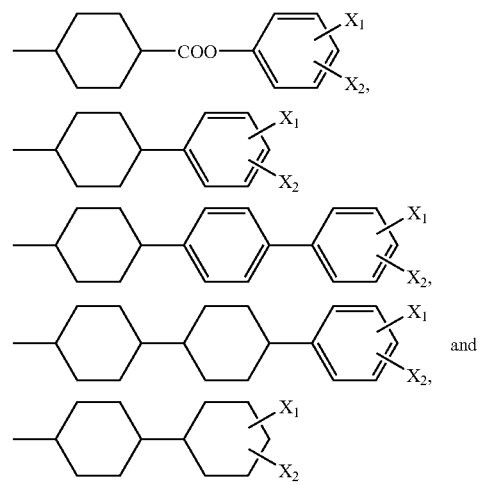

wherein $X_1$ and $X_2$ are each independently —H, —$CH_3$, —$CF_3$, —F, —Br, —Cl, —CN, —OH, or —$NO_2$.

2. A polyamic acid prepared by reacting a diamine component (a) and an acid dianhydride (b), the diamine component including 0.1 mole % or above of the diamine compound according to claim 1 based on 100 mole % of the diamine component, and the polyamic acid having a repeating unit represented by Formula 2 below:

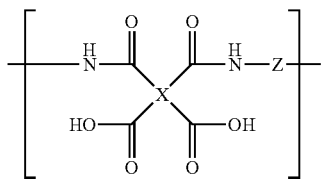
(2)

wherein x is a tetravalent aromatic or alicyclic organic group, and z is a divalent organic group originating from the diamine compound of Formula 1.

3. The polyamic acid according to claim 2, wherein the diamine component (a) further includes an aromatic diamine compound and a polysiloxane-based diamine compound represented by Formulae 3 and 4 below, respectively:

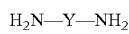
(3)

wherein Y is a divalent aromatic organic group,

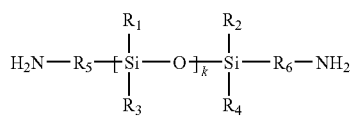
(4)

wherein $R_1$, $R_2$, $R_3$ and $R_4$ are each independently a $C_{1-10}$ alkyl, alkoxy or aryl group, and $R_5$ and $R_6$ are each independently a $C_{1-10}$ alkylene group.

4. The polyamic acid according to claim 3, wherein the substituent Y in Formula 3 is a divalent organic group selected from the group consisting of the following groups:

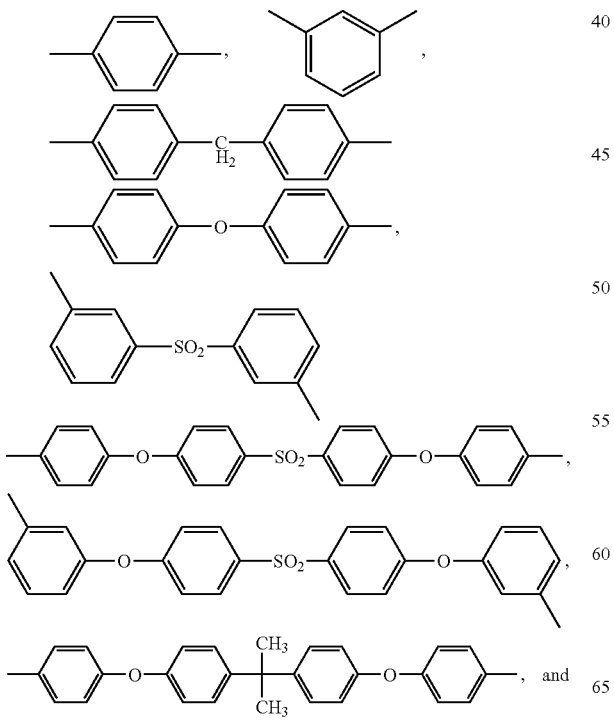

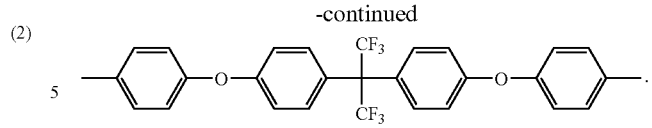

5. The polyamic acid according to claim 2, wherein the acid dianhydride component (b) is an aromatic cyclic acid dianhydride represented by Formula 5 below:

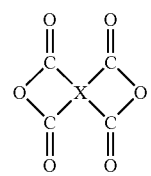
(5)

wherein X is a tetravalent aromatic cyclic organic group; an alicyclic acid dianhydride represented by Formula 6 below:

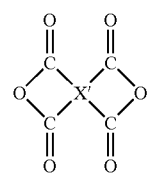
(6)

wherein X' is a tetravalent alicyclic organic group; or a mixture thereof, the mixing molar ratio of the aromatic cyclic acid dianhydride to the alicyclic acid dianhydride being between 1:99 and 99:1.

6. The polyamic acid according to claim 5, wherein the substituent X in Formula 5 is a group selected from the following groups:

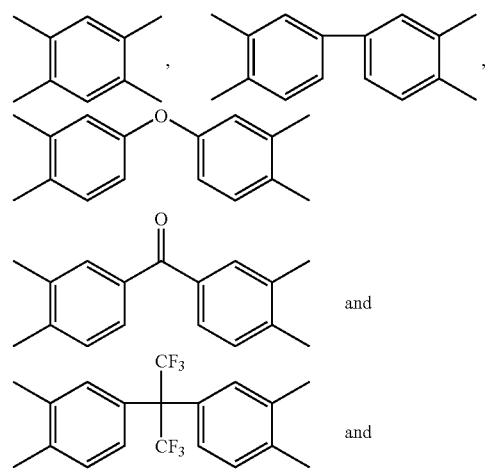

the substituent X' in Formula 6 is a group selected from the following groups:

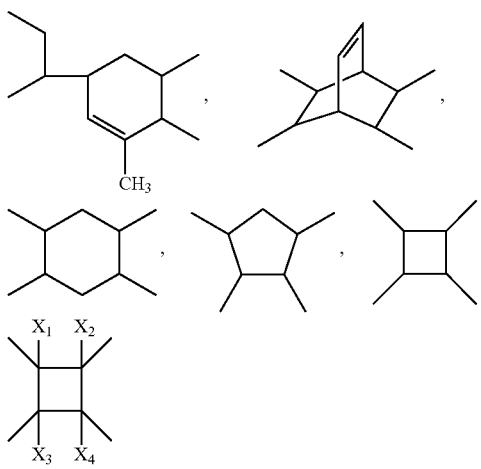

wherein $X_1$, $X_2$, $X_3$ and $X_4$ are each independently —H, —$CH_3$, —$CF_3$, —F, —Br, —Cl, —CN, —OH, or —$NO_2$.

7. The polyamic acid according to claim 2, wherein the polyamic acid has a number average molecular weight ranging from 10,000 to 500,000 g/mol.

8. A liquid crystal aligning agent comprising the polyamic acid according to claim 2.

9. A liquid crystal alignment film produced by coating the liquid crystal aligning agent according to claim 8 onto a substrate, and entirely or partly imidizing the coating.

10. A liquid crystal display device comprising the liquid crystal alignment film according to claim 9.

11. The diamine compound of claim 1, wherein A is —O—, B is a direct bond, and C is a $C_{1-30}$ linear aliphatic hydrocarbon group.

12. The diamine compound of claim 11, wherein said compound is

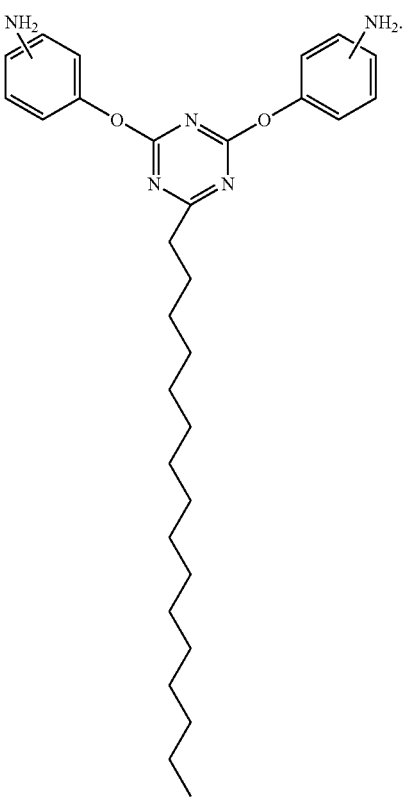

* * * * *